(12) United States Patent
Saadat et al.

(10) Patent No.: US 8,463,359 B2
(45) Date of Patent: Jun. 11, 2013

(54) SHAPE-SENSING EXPANDABLE MEMBER

(75) Inventors: Vahid Saadat, Atherton, CA (US);
Zachary J. Malchano, San Francisco, CA (US)

(73) Assignee: Nidus Medical, LLC, Atherton, CA (US)

( * ) Notice: Subject to any disclaimer, the term of this patent is extended or adjusted under 35 U.S.C. 154(b) by 656 days.

(21) Appl. No.: 12/109,175

(22) Filed: Apr. 24, 2008

(65) Prior Publication Data

US 2009/0005674 A1 Jan. 1, 2009

Related U.S. Application Data

(60) Provisional application No. 60/914,014, filed on Apr. 25, 2007.

(51) Int. Cl.
*A61B 5/055* (2006.01)
*A61B 8/14* (2006.01)
*A61M 29/00* (2006.01)

(52) U.S. Cl.
USPC .................. 600/424; 600/466; 604/99.01

(58) Field of Classification Search
USPC ............... 600/407, 424, 448, 462, 466, 507; 604/96.01, 98.01, 99.01
See application file for complete search history.

(56) References Cited

U.S. PATENT DOCUMENTS

| | | | | |
|---|---|---|---|---|
| 5,797,849 A | * | 8/1998 | Vesely et al. ................. | 600/461 |
| 5,865,801 A | * | 2/1999 | Houser ................... | 604/103.07 |
| 2005/0251032 A1 | * | 11/2005 | Smith .......................... | 600/433 |
| 2010/0113939 A1 | * | 5/2010 | Mashimo et al. ............. | 600/470 |

* cited by examiner

*Primary Examiner* — Michael Rozanski
(74) *Attorney, Agent, or Firm* — Levine Bagade Han LLP (57) ABSTRACT

An expandable member for characterizing a three-dimensional space within a mammalian body is described. The expandable member is delivered to a target region in a deflated state where it is expanded by inflation of the member. Sensory transducers that contact the member relay sensory information generated when the member is in an expanded state to a microprocessor located outside the body. Using the sensory information, a data-driven picture that characterizes the three-dimensional space within the body is created with a microprocessor. The apparatus is useful in preparation for minimally invasive surgical therapy.

26 Claims, 7 Drawing Sheets

FIG. 7B

SHAPE-SENSING EXPANDABLE MEMBER

CROSS-REFERENCE TO RELATED APPLICATIONS

This application claims priority to U.S. Prov. Pat. App. 60/914,014 filed Apr. 25, 2007, which is incorporated herein by reference in its entirety.

FIELD OF THE INVENTION

The present invention relates generally to a minimally invasive medical apparatus for determining characteristics of a space within a mammalian body and methods of using this apparatus.

BACKGROUND OF THE INVENTION

Minimally-invasive surgical procedures and interventions reduce recovery time and post-operative pain by reducing the size of the incision and intra-operative blood loss. However, due to the nature of minimally invasive procedures a physician typically relies on additional technology to gather the needed information about the target location while conducting the procedure. Current technology to support visualization during minimally invasive procedures includes imaging systems in the visual light spectrum, ultrasound imaging, infrared imaging, and x-ray imaging.

A major limitation of many of these visualization technologies is their inability to characterize the space within the body. Many of these systems image two-dimensional planes or create two-dimensional projections of a three-dimension object, and therefore the information that is conveyed back to the practitioner can be of limited use or is inaccurate with respect to the three-dimensional character of the space. Other systems provide visualization of a space by picturing the walls of the space, without an ability to convey the volume information of the space confined by the walls.

SUMMARY OF THE INVENTION

One problem addressed by the invention is the problem inherent in placing a medical implant or performing a treatment within the body using a minimally invasive procedure. It is advantageous to know the precise three-dimensional parameters (for example, space and volume) of the target region into which, e.g., the implant is to fit. After learning the three-dimensional parameters, a practitioner can select the proper size of implant, or design an appropriately sized and shaped implant specifically for that target region. One variation is an apparatus to gather information that results in an accurate characterization of the three-dimensional parameters of a target region having a volume. Methods of conducting such an assessment and systems for conducting the assessment are also contemplated within the scope of the invention.

The patient to whom the invention can be applied can be any animal, preferably a mammal, and most often, typically, a human patient. The device implants that are the object of the minimally invasive procedure supported by the invention can be selected from, for example, stents, valves, and other internal prosthetic devices. The implants can also be biotherapeutic agents in semi-liquid or semi-solid form for use in filling the target space.

One example of an apparatus is a space-sensing expandable apparatus deliverable in a deflated and unexpanded state to a target region having a volume, whereupon it is inflated or expanded in the target region. Sensory data from transducing sensors in the apparatus is collected and the device is deflated and removed.

The expandable apparatus is typically delivered over a guidewire, and also can be delivered within a catheter delivery sheath (optionally also over a guidewire, the catheter optionally steerable). In any case, after receiving the three-dimensional data from the expandable apparatus in the target region, the space-sensing apparatus can be removed and replaced (e.g. over the wire) with the implant device, or a biotherapeutic agent. For example, over the same guidewire a stent can be delivered within a catheter and deployed at the target region. Alternatively, an agent can be delivered through an infusion lumen in a delivery sheath.

After receiving the sensory information from the inflated expandable device and after processing that information, an implant customized for the target region, or one otherwise appropriate for the target region, can be selected and delivered to the target region. By example, a stent, occlusion device, or other prosthetic can be selected to fit the target region and delivered to the region and deployed. Also by example, where a biotherapeutic material (e.g. a gel or therapeutic emulsion) is to be delivered to a target region, the expandable apparatus may provide sufficient information as to the volume of the space so as to know how much of the semi-solid agent is needed to fill the region. Thus, the apparatus is a useful adjunct for any minimally invasive surgical therapy or other minimally invasive procedure, especially where the procedure is better facilitated by knowing the size of the space into which the implant is directed.

The apparatus comprises an expandable member that can be inflated within the body using, for example, an inflation lumen for infusing fluid or gas into the expandable member. Thus, the member can be an expandable member such as a balloon adapted to expand by inflation of liquid or gas. The expandable member is delivered in a deflated state to the target region. The expandable member may be compliant so that the shape it takes on upon inflation can conform to the space of the target region. Optimally, the inflated expandable member may substantially fill a volume of the space at the target region, in order that the dimensional information relayed about the space is as accurate as possible.

Conformation of the inflated expandable member in a target region is where the outside surface of the expandable member contacts one or more points of the tissue defining the space. Thus, in order to ensure that the expandable member contacts one or more points that define the space within the target region, the expandable member may be at least as large, or optimally slightly larger (upon inflation) than the space within the target region. In practice the member is inflated to the limits of the space and sensory information taken at the point of maximum inflation within the space. If the expandable member is too small it will not be able to conform to the target region with sufficient precision to convey accurate information about the three-dimensional character of the target region. If the member is larger than the target space, it will not reach its maximum capacity, but will stop filling when its volume equals the volume of the space. Thus, the expandable member is preferably adaptable to slightly exceed the volume of a target region, which assures that the member will conform to the space when inflated in the body. In this way, the expandable member being expanded can contact the sidewalls of the cavity or space, and the most accurate determination of the volume of the space can be determined. By contacting the peripheral limits of the cavity, the sensory transducers located both within and outside the member can sense the volume of the space and relay that sensory information to a microprocessor located outside the body and available for that purpose.

The apparatus comprises an expandable member having sensory transducers, the majority of which are located within the expandable member, but at least one of which may be located outside the expandable member (e.g. outside the surface of the member) depending on the type of sensory information the system is working under, on the outside surface of the member. The transducers relay information to a microprocessor residing outside the patient's body. A transducer within or outside the expandable member senses contact of the member with the peripheral walls of the space and communicates with at least one other transducer on the apparatus in order to send feedback to the microprocessor outside the body.

There are several ways that the transducers can collect and relay their information, including electrical impedance measurement through a conductive medium, ultrasound transmitting through a conductive medium, optical transducers, and low-field electromagnetic sensors. Where the sensing mechanism is by electrical impedance, the apparatus also has at least one temperature sensor to maintain a constant temperature in the conductive medium, as temperature change affects electrical impedance measurements.

The expandable member is expanded, typically by inflating the member with fluid or gas, preferably a fluid or gas that enables or assists the transduction of information from one transducer to another, as the fluid or gas is generally in contact with the transducers. For example, sodium chloride in aqueous solution (e.g. saline) as a conductive medium, may be utilized for filling the expandable member if the transducers gather and relay their information by electrical impedance. If the transducers transmit information via ultrasound, then the expandable member will be filled most optimally with a medium that allows conduction of ultrasonic waves.

Once the apparatus is placed in the target region and expanded, the transduction mechanisms allow for the accurate determination of the distance between any two sensors. With multiple transducers sensing distances between multiple other transducers, a picture of the volume and space of the region can be developed. For the purpose of relaying sufficient information to a microprocessor to generate an accurate picture of the space and volume of the target region, the expandable member will have a plurality of transducers positioned within the member or outside the member. In some embodiments, the apparatus will most optimally have several internal transducers, and at least one external transducer. Each transducer relates to at least one other transducer within the expandable member or to the one or more external transducers, so that information regarding such parameters as the distance between two transducers can be relayed to a microprocessor. Optimal sampling of information may be achieved where every transducer communicates with every other transducer to develop sufficient sensory information so that accurate characterization of the three-dimensional space within the target region is achieved.

The apparatus will have a microprocessor located outside the body that has a mechanism for recording information captured from the transducers including details that contribute to a deduction about the shape of the target region, the volume of the target region, display of the shape information (for example display of a picture on a computer screen), similar display of the volume information (e.g., as a 3-D image on a computer screen), measurement of specific data such as surface curvature, distance and volume between transducers, and subtracting an initial data set from a subsequent data set to identify a change in shape or volume or other parameter. The computer will have the necessary software and hardware to receive and interpret the transducer sensory information to provide a user friendly interface and near immediate conveyance of synthesized data for use by the practitioner.

The transducers yield their information by reference to a reference sensor also located on or near the expandable member. Typically, the transducers will measure at a minimum a distance from one transducer to another transducer, and optimally also additional information.

The system will also optimally be calibrated so that the sensory information has a reference value. Calibration comprises developing a known set of data points against a known distance (or other calibration parameter), which establishes a reference point for measurements from the transducers that are not within the calibration zone. The calibration zone is for use as a reference point against which the accuracy and specificity of the real time measurements from the transducers can be determined. The calibration zone can be included within the apparatus as part of it. The calibration zone can be an area or volume which is fixed, and therefore, it would not change when the apparatus is inserted into a cavity within the body, or with inflation of the expandable member. The other measurements from the transducers are adjusted by a calibration factor developed in the calibration zone.

The expandable member can be adapted to slide over a guidewire for delivery to the target region over a through-lumen in the expandable member. Alternatively, or in addition, the expandable member can be adapted to fit within a steerable catheter for delivery to the target region. Accordingly, after the expandable member has conveyed the space and volume information to the computer, the member can be withdrawn (also over the guidewire and/or within the catheter sheath) so that the guidewire remains and can be used for delivery of an implant device, or therapeutic material.

The apparatus may typically have mechanisms for controlling various aspects of the apparatus. Mechanisms for controlling the apparatus elements may typically reside outside the body during any such minimally invasive procedure. One type of controlling mechanism is a handle external to the body. A control mechanism can be available to the system for controlling various aspects of the apparatus such as steering the expandable member to the target region, inflating the member with air or fluid such as saline and also deflating the member and withdrawing the member. In addition, a control mechanism can control or readjust transducer position in some or all of the transducers. It is possible that the apparatus will be positioned in the space of the target region, and expanded, and a first set of readings taken from the transducers. Thereafter, some slight repositioning of the apparatus can occur, in order to take another set of measurements that can be averaged with the first set. The handle, or other control means, can be used to facilitate this movement of the apparatus, and request for a second (or subsequent readings) from the transducers.

In some embodiments, it may be desirable to maintain control on the degree of inflation of the member, e.g. if the cavity or space is expanding, for example during labor in childbirth. In this instance, the apparatus may include mechanisms for maintaining an expanding pressure on the expandable member, particularly while the space itself is expanding. Accordingly, the apparatus could be configured to maintain a certain expanding pressure on the expandable member. With the maintenance of pressure on the space by continuously (albeit slowly) inflating the expandable member, the apparatus can maintain its position within a space that is expanding, even while it continues to relay information about the volume of the space to the microprocessor. An apparatus with this continuously expanding capability could be placed at the cervical opening during child birth to monitor the cervical dilation preceding vaginal delivery.

Another usefulness of the ability of the apparatus to maintain and increase the inflation on the expandable member would be to exert pressure in a space and cause desired physiological response thereby. For example, the inflating apparatus could be used not only to measure an expansion of the cervical or vaginal space, but also to gently expand the cervix to minimize the undesired side effects of perennial lacerations which can occur when the cervix expands quickly.

If the apparatus uses electrical impedance to determine the distances between the transducers, the apparatus may include a mechanism to determine the temperature of the electrolytic solution or a mechanism to maintain a constant temperature of the electrolytic solution. The resistivity of an electrolytic solution changes with temperature; therefore these temperature variations should be known or controlled. One method to minimize temperature variations would be the constant circulation of the electrolytic solution through a heater or chiller to maintain a set temperature via a feedback system. A second method of assessing and compensating for temperature variations would be the addition of temperature sensors (thermistor, thermocouple, optical temperature sensing) within the lumen of the expandable member. Using temperature measurements obtained from these units, a calculation could be made to calculate the resistivity of a known concentration of electrolyte within the solution, which in turn affects the value accorded the sensory information received from the transducers.

The transducers can operate and communicate by low-field electromagnetic sensing. The transducers can be internal coils placed in the expandable member relative to an external magnetic field positioned outside the body. The conveyance of the electromagnetic information can be accomplished by making a determination of a position and orientation between internal coils and the external magnetic field.

The apparatus may be used in a method for assessing the precise three-dimensional parameters (for example, space and volume) of the target region into which an implant is to fit. The method may include introducing into a body a deflated expandable member adapted to expand within the body (such as just described), and navigating the deflated expandable member to a target region in the body. Once in the target region the expandable member is inflated, e.g., with saline. The member has a plurality of transducers within it, and may have one or more outside it, for conveying information back to a central microprocessor located outside the body. The microprocessor outside the body receives the information from the transducers and processes it. The transducers are used to determine data in relation to at least one other transducer, and also with reference to a reference sensor. So, for example one transducer relays information relative to another transducer. The information can be a relative distance between transducers, or other such useful information. The transducer functioning is generally dependent on reference to a calibration made also within the apparatus, so that distance or other information between two transducers can be given relative weight with reference to the calibration data.

The target region in the method can be any region in the body accessible by navigation through a body lumen in a minimally invasive procedure. Also, a target region can be a region accessible in a body orifice through either physician placement or apparatus-assisted access. Typical procedures may be by intravascular access. Some exemplary regions in the body to which the apparatus can be directed include the heart, the abdominal aorta, the spinal column, and a body orifice or an organ having a tumor.

In the heart, for example, measuring the shape of the left atrial appendage could be useful for the sizing and placement of left atrial appendage occlusion devices. Measurement of the shape and size of the pulmonary vein ostia could be useful for the sizing of ablation modalities which use expandable members or other fixed shapes during pulmonary vein isolation procedures to eliminate atrial fibrillation. Measurement of the size and shape of the septal defects in the atrium or ventricle could be useful for the sizing and positioning of septal defect closure devices (such as the Amplatz apparatus).

The apparatus could also be used to measure or assess the extent of an aneurysm such as an abdominal aortic aneurysm (AAA). The apparatus can measure or determine the shape and volume of a space in or around the spinal column for use during minimally-invasive treatments of spinal stenosis. The apparatus could also be used to assess the extent of a resection to remove a tumor (benign or malignant) in the breast, liver, prostate, or other organ or tissue. Currently the extent of a suspected tumor can be determined pre-operatively using imaging technology (computed tomography x-ray or magnetic resonance imaging); however, within the operating room, the extent of resection is determined visually and with serial frozen sections processed by the surgical pathologists. The shape sensing expandable member could be used to assist in the removal of this tissue by providing a measurement of the shape and volume or extent of the cavity remaining following the resection procedure.

The apparatus may also include a system for accurate characterization of a three-dimensional space within a body comprising a delivery sheath for the expandable member as described above, and a microprocessor for receiving and analyzing the information. The system can further include control members for controlling one or more functions of the process of using the expandable member (e.g. steering the delivery catheter to deliver it, inflating the member, deflating the member and adjusting the transducers). Control member or members can be embodied in a handle, or other such mechanism for steering, manipulating, positioning, inflating, deflating, and relaying transducer signals. The system can further comprise a guidewire that can fit within a through-lumen of the expandable member. The expandable member may be delivered to the target region over the guidewire, or within a steerable catheter, or both.

Additionally, the microprocessor can include a mechanism for recording captured information. The information can be, for example, a shape of the target region, a volume of the target region, display of shape information, display of volume information, display of captured information over time, measurement of specific data such as surface curvature, distance and volume, subtracting an initial data set from a subsequent data set, and display of any and all this information in a user-friendly format.

DETAILED DESCRIPTION OF THE INVENTION

Figure 1A:
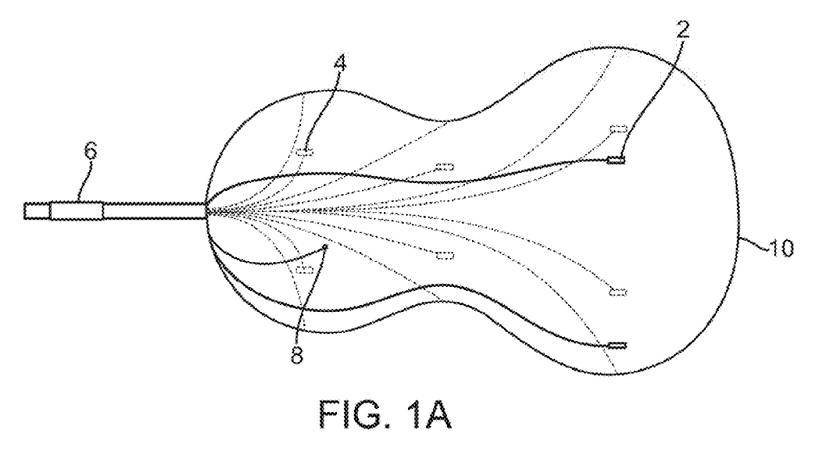
FIG. 1A shows a side view of close-ended elliptoid-shaped expandable member.
Figure 1B:
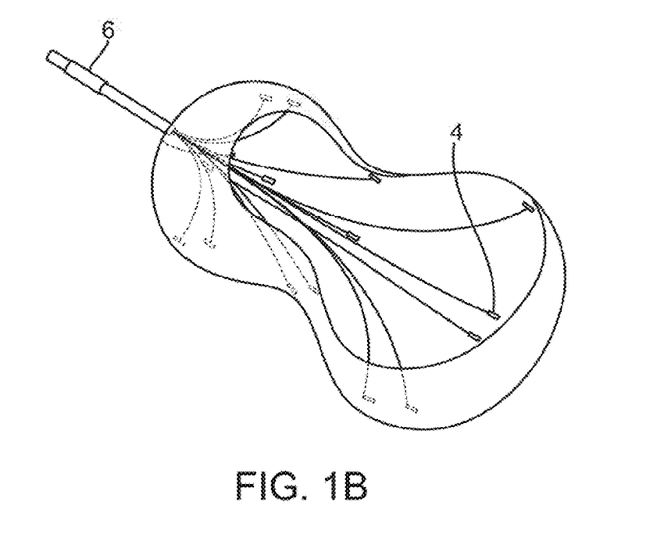
FIG. 1B shows a partially disassembled perspective view of the same expandable member.

FIGS. 1A and 1B show side and perspective views, respectively, of an expandable member 10 in its inflated state. Expandable member 10 may be made out of highly distensible elastomeric compliant material such as latex, an elastomeric block copolymer, or a thermoplastic elastomeric material, and therefore adapted to inflation with fluid or gas. The expandable member 10 can also be made out of other materials that are non-compliant, such as PET (polyethylene terpthalate), polyurethane or silicone. In this case, where the material is not expandable the member may have excess material when deflated and that material is fillable with the fluid or gas infusion medium. Expandable member 10 is generally designed to be conformable to the shape of a hollow body cavity, and will in any event occupy a three-dimensional space upon expansion. In order that the expandable member optimally sense the volume and other three-dimensional characteristics of the space within a target region of the body, the expandable member should expand to a volume roughly equal to the space at the target region. Thus the proper size of the expandable member 10 should be selected based on estimation of the expected volume of the space within the target region. Accordingly, for any given procedure a practitioner may have several different sizes of expandable members available for use, in order to select the most appropriate size based on estimates before a procedure.

The expandable member 10 is illustrated in this example as having an elliptoid shape. Other shapes of expandable member are possible including ovoid, spheroid, elongate, or other uniform shapes as well as irregular shapes. Inflated expandable member 10 has a plurality of transducer sensors 4 positioned on an internal or external surface of the member. Additional transducer sensors 2 may also be positioned on the internal or external surface of member 10 provided that the expandable member 10 has sensors positioned over its length. In this variation, sensors 2 are illustrated as located along the external surface of apparatus. Sensors 2 and 4 are electrically coupled to a reference sensor (not shown) by a conductive wire or fiberoptics. FIG. 1B depicts an apparatus with the member covering partially cut away for clarity. The transducer sensory electrodes can be made from gold, silver, platinum or other conductive metals. The conductive wires that lead to and connect with the transducer sensors can also be made out of gold, copper, etc. Preferably the metal will be compatible with body fluids, which may be particularly important with any transducer sensors that contact body fluids.

In this and other variations herein, the plurality of sensors may be included along the internal and/or external surfaces of the member or even integrated within the member material itself. Moreover, the sensors may be positioned along the member 10 at uniform distances longitudinally from one another as well as uniform distances over the member circumference between adjacent sensors. Alternatively, sensors may be positioned at non-uniform distances from one another longitudinally as well as circumferentially. Additionally, the cumulative number of sensors positioned upon member 10 may be varied depending upon the volume or void to be measured although the increased number of sensors may result in increased accuracy of volume or void measurement.

Normally the expandable member 10 may be inflated using a conductive fluid, such as saline, with a known resistivity. The resistivity of the conductive fluid is measured in situ by using the reference transducer sensors 6 which has a fixed distance between them. By knowing the resistance between the reference transducer sensors, the resistivity of the fluid can be established. Thereafter, by measuring the resistance between any pair of transducers within the member 10 and knowing the resistivity of the fluid within the member 10, one can establish the distance between any pairs of transducers. By determining the plurality of distances between the pairs of transducer sensors, a shape collectively defining the contour of the expandable member, upon which these transducer sensors are positioned, can be determined.

There may be additional external transducer sensors that are placed, e.g., on the external surface of expandable member 10. These sensors may be connected to an outside source (not shown), which could also include an electrostimulation apparatus. These transducers can be optionally used to stimulate the wall of a cavity within which they are placed, such as inside the chambers of a mammalian heart.

As shown in FIG. 1A, expandable member 10 can also include a temperature sensor 8 to track the temperature of the inflation fluid. As the resistivity of the conductive fluid contained within the expandable member 10 can change as a function of temperature, measurements of the temperature of the fluid may be utilized so that the resistance readings can be normalized.

Once the shape of the inflated expandable member 10 as it is positioned in the three-dimensional space is established mathematically, the shape information can be displayed on a computer screen for user-friendly visualization and manipulation of the resulting image or images. Additionally, if a procedure requires a before and after measurement of a shape, such as when tissue is removed from the cavity, the system can display the difference between the shape pre- and post-procedure to establish the difference between the two and allow the operator to use that information to determine the amount of tissue that has been removed. Computer and data-acquisition systems as known to those skilled in the art are used to both acquire and display the information.

Figure 2A:
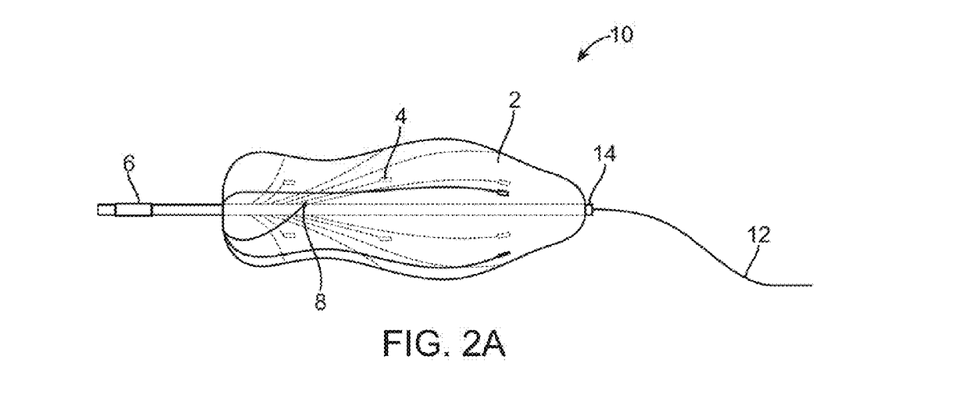
FIG. 2A shows a side view of through lumen expandable member.
Figure 2B:
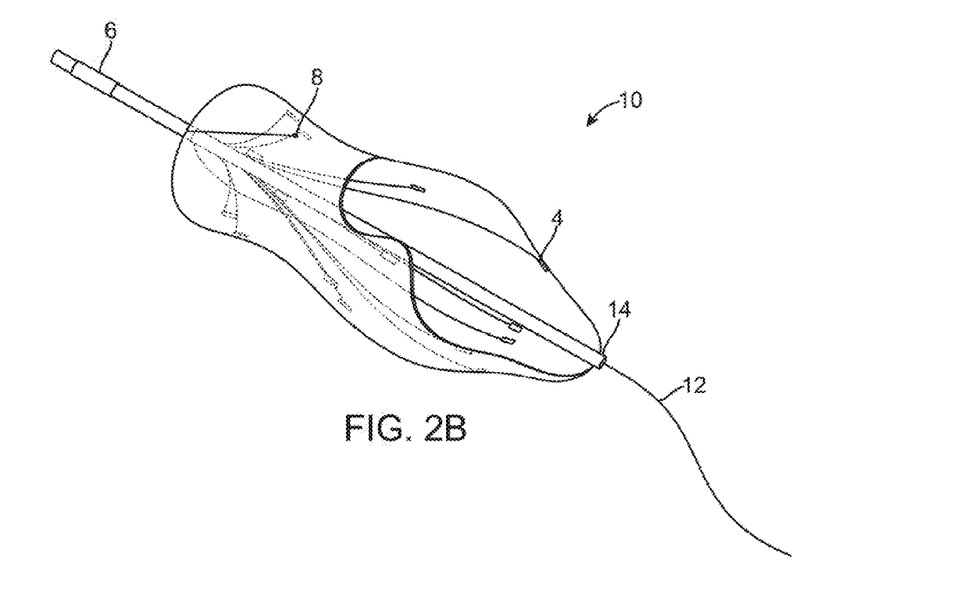
FIG. 2B shows a partially disassembled perspective view of the same expandable member.

FIGS. 2A and 2B show side and perspective views of another variation of an inflated expandable member 10 having a through-lumen 14 for passage of guidewire 12. The member 10 can be slid over guidewire 12 to guide the apparatus to the target region. Sensors 2, 4 and reference sensors 6 as well as the temperature sensor 8, are also shown. Expandable member 10 is delivered over guidewire 12 to a target region, and can be inflated while remaining on the guidewire 12. After the plurality of transducers 2 and 4 have relayed sensory information back to a microprocessor, the member 10 can be deflated and withdrawn (preferably within a delivery sheath—not shown) over the guidewire 12. The guidewire 12 may be kept in place for delivery of the implant device, biotherapeutic materials, or other instruments.

Figure 3:
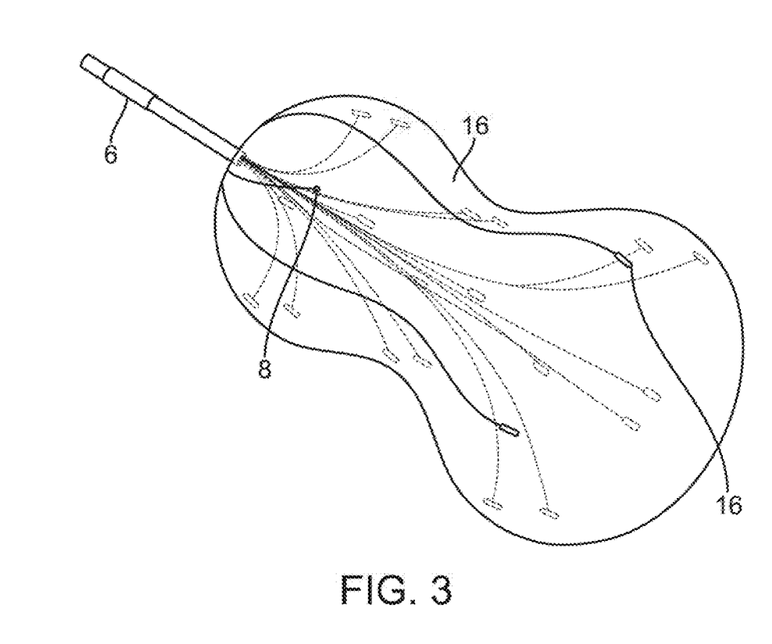
FIG. 3 shows a perspective view of a shape sensing expandable member utilizing ultrasound.

FIG. 3 shows an ultrasound shape sensing expandable member having a plurality of ultrasonic transducers 16 over the inflated expandable member 10. As the inflation fluid can transmit ultrasonic energy efficiently, by measuring the time-of-flight or delay time of an ultrasonic pulse between a pair of transducers 16, the distances between the pairs of transducers 16 can be established, and a computer system can be used to acquire and display this information. A temperature sensor 8 and a pair of reference transducer sensors 6 can also be included. A through-lumen and external stimulating sensors can also be included as depicted in FIGS. 1A and 1B, but not shown here.

Figure 4A:
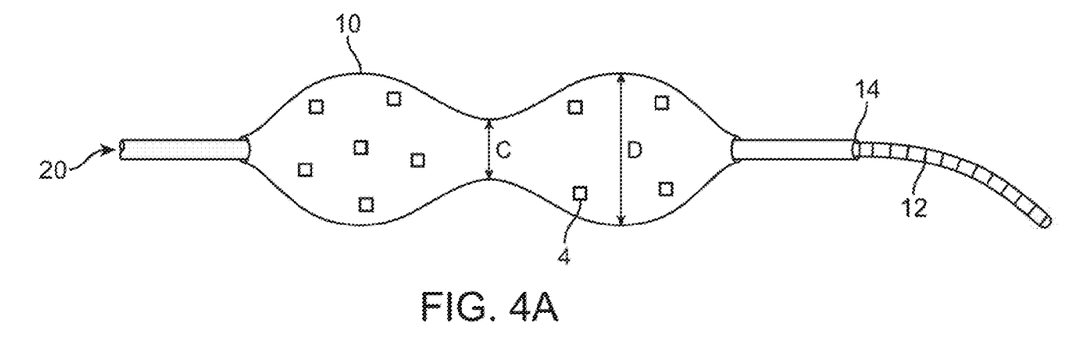
FIG. 4A shows a side view of a variation of the shape sensing expandable member showing the expandable member's position before the procedure.
Figure 4B:
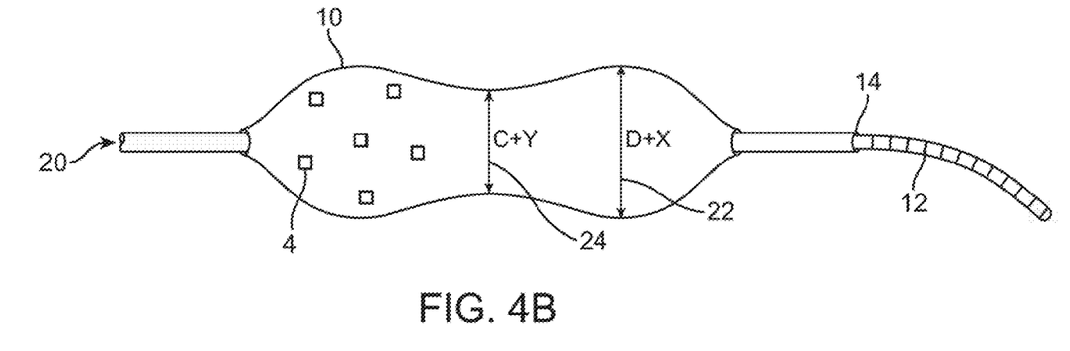
FIG. 4B shows a side view of a variation of the shape sensing expandable member showing the expandable member's position after the procedure.

FIG. 4A depicts a side view of a variation of the deflated expandable member 10 before delivery to a target region where an initial diametric (or circumferential) distance along a first location of member 10 is indicated as measuring a distance "C" and an initial diametric (or circumferential) distance along a second location of member 10 proximal to the first location is indicated as measuring a distance "D". FIG. 4A includes through-lumen 14, and transducing sensors 4. FIG. 4B depicts the same apparatus as depicted in FIG. 4A, but after a procedure, upon removal from the body. As shown, the increase in diameter (or circumferential distance) along the first 22 and second 24 locations is shown as an increase C+Y and D+X, respectively. In this manner, changes in the diameter or circumferential distance over multiple locations along the length of the member 10 may be detected by the differential movement between sensors and calculated to result in a distance change.

Transducing sensors 4 are present within both the deflated and inflated expandable member 10. Guidewire 12 may be optionally placed within through-lumen 14. In FIG. 4B dimensions 22 and 24 indicate the shape and dimension of the body cavity that the apparatus was placed within. In both FIGS. 4A and 4B fluid infusion is directed at point 20 through a lumen that accesses the internal portion of the expandable member 10. Visual comparison of apparatus 10 in FIG. 4A as compared to FIG. 4B demonstrate an expansion of the apparatus by inflation which is captured as information depicted in the greater distances show in the spans 22 and 24.

Figure 5A:
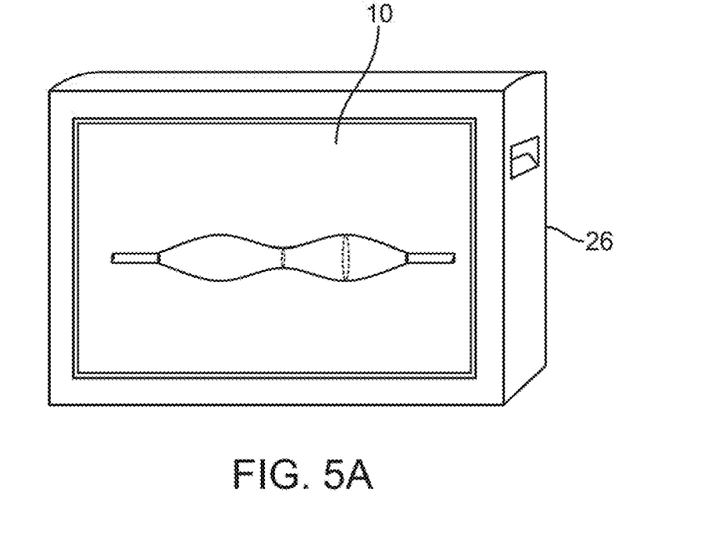
FIG. 5A shows the expandable member contour before procedure which is illustrated on the monitor.
Figure 5B:
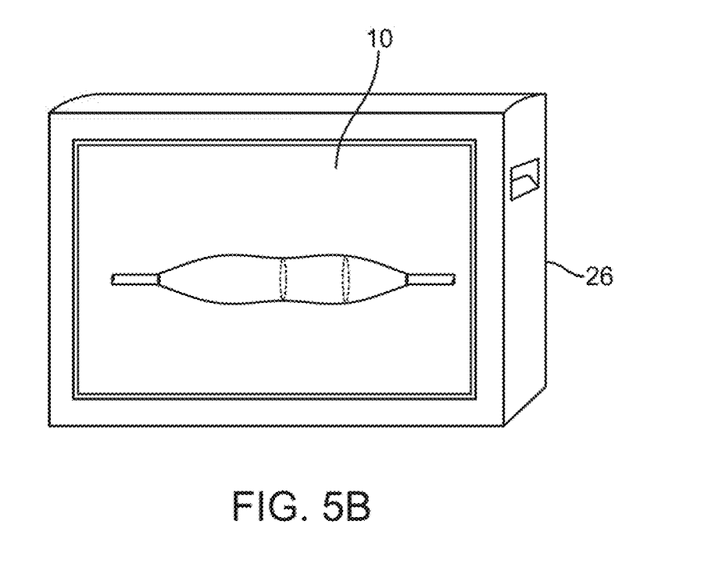
FIG. 5B shows the expandable apparatus contour after procedure which is illustrated on the monitor.
Figure 5C:
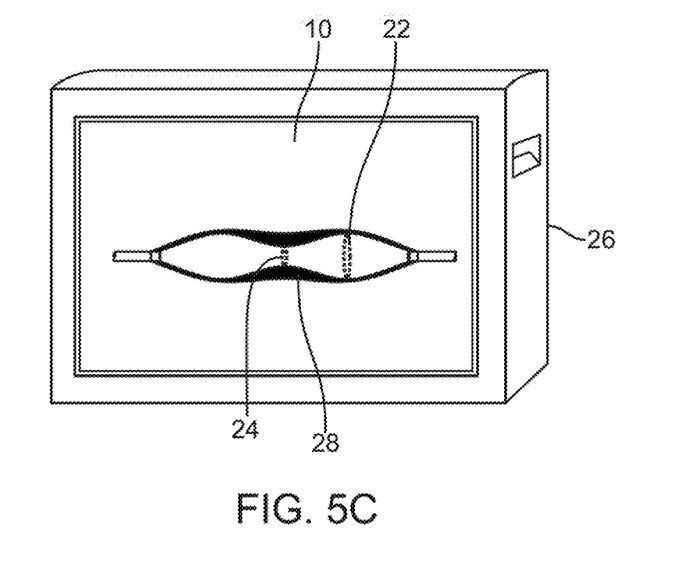
FIG. 5C shows the volume change in the expandable apparatus which indicates by the blackened area.

FIG. 5A depicts the expandable member 10 in its contour in a deflated state before a procedure as visually mapped in a corresponding manner on a representative member 10 on a computer monitor 26. FIG. 5B depicts the expandable member 10 in its expanded or inflated state. FIG. 5C depicts the differential volume change 28 between the deflated state (shown in FIG. 5A) and inflated state (shown in FIG. 5B) of the expandable member 10 as a visual function on monitor 26. The resulting comparative region 28 can be quantified using a computer program to extrapolate a value for the change in volume in three-dimensional space from the deflated to inflated state of the expandable member.

Figure 6:
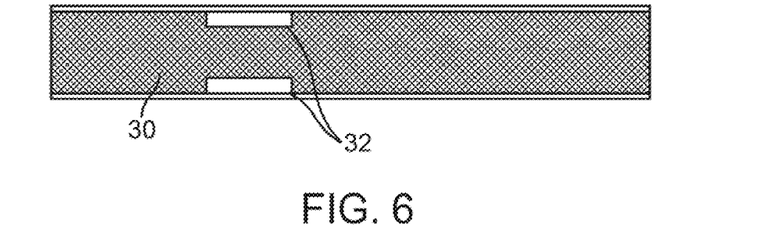
FIG. 6 shows a pair of sensory transducers which can be employed to measure the resistivity or other parameter of the fluid within the lumen to serve as the reference when measuring the distance between other pairs of sensory transducers.

FIG. 6 depicts a partial cross-sectional side view of reference sensor sensors 32 residing in a saline filled lumen 30. A pair of transducer sensors 32 is employed to measure the resistivity or other parameters of the fluid within the lumen 30 to serve as the reference when measuring the distance between other pairs of transducer sensors. Systems such as those depicted in FIG. 6 can be the basis of a calibration tool against which the distances of the other transducer sensors in the apparatus can be determined.

There are many applications in a human body that can benefit from a shape-sensing expandable member 10. For instance, the expandable apparatus can measure the anatomy and size of the chambers of the heart, much like a CT scan, without the use of x-rays. This information can be used to guide procedures, such as atrial fibrillation treatment, valve replacement and atrial septal defect therapies, etc. Prior to replacing a valve, such as the mitral valve or the aortic valve or the tricuspid valve, the expandable member can be inflated and the size and morphology of these valves can be accurately measured. The physician then has the opportunity to choose the right size valve for the procedure.

Other applications for the apparatus may also include spinal stenosis therapy, during which a surgeon removes a portion of tissue that is impinging upon a peripheral nerve. The method of using the shape-sensing expandable member 10 in this case includes passing the member 10 over a guidewire 12 into the spinal foramen before operating on the region to assess the shape and the size of the lumen under a fixed pressure. The expandable member 10 is removed after conveying three-dimensional information to a microprocessor. Thereafter, offending tissue is removed from the foramen and thereby creating more space to relieve pressure on the nerve. At that point, the expandable member can be reinserted into the foramen, and the post-operative size of the foramen can be measured again under the same pressure as before. The difference between these two measurements (which equals the amount of tissue that was removed by the surgeon) can serve as an indication of the success of the procedure, and a confirmation that sufficient tissue was removed to relieve the peripheral nerve.

The apparatus can also be used to conduct procedures such as optical interferometry which is also called a time-domain reflective technique. With this technique, a distance between a light source and a sensor (the sensor located on a fixed portion of the expandable member such as an axial shaft within the expandable member 10) and a reflective portion on the surface of the shape-sensing expandable member is determined. As the sensor reflective portion expands away from the sensor, that information is captured as a change in distance. These measurements, although extremely fast, facilitate design choices that can be made by physicians based on the path that the light takes to the reflective sensor.

Figure 7A:
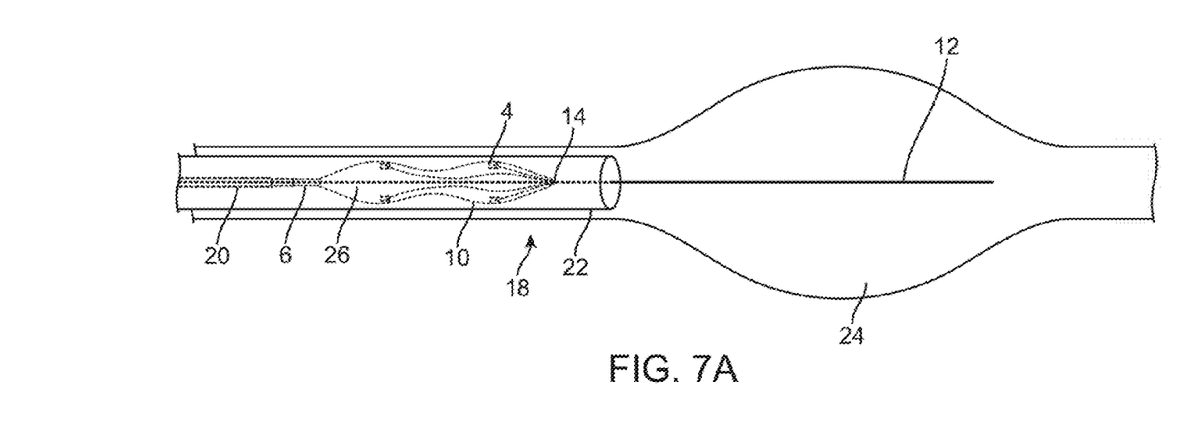
FIGS. 7A and 7B depict a delivery system for delivering the apparatus to a target region in a vessel.

Aside from uses, in delivering the expandable member 10 to a void or space within the body, a delivery sheath may be optionally used for delivery and/or deployment. For instance, FIG. 7A depicts a partial cross-sectional side view of delivery system 18 for delivering the expandable member 10 to a target region 24. Guidewire 12 may be advanced through lumen 14 defined through member 10 and into the targeted region 24. Delivery sheath 22 may retain deflated member 10 during delivery through the tissue space.

Figure 7B:
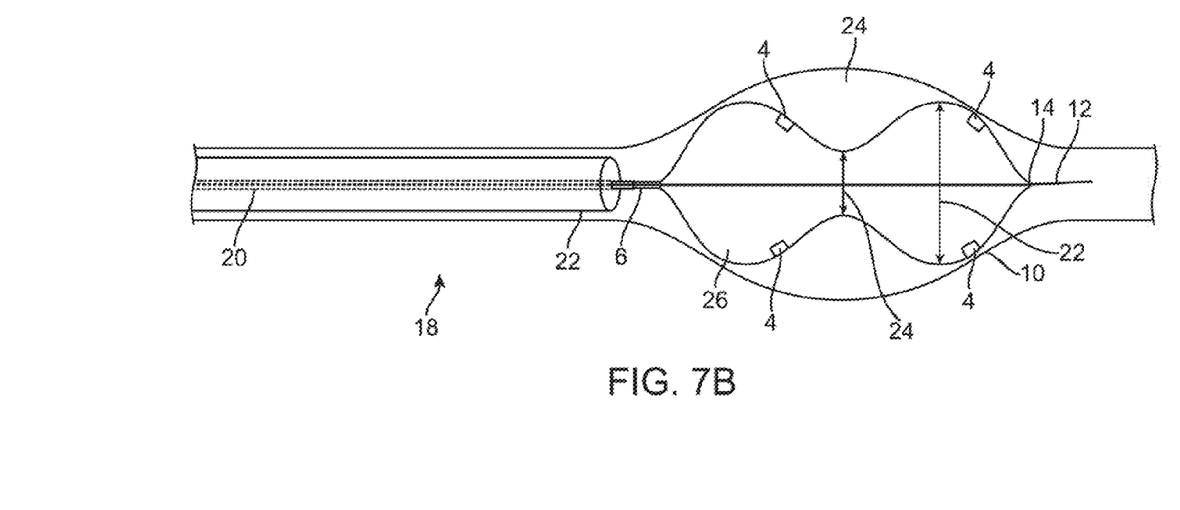

As shown, reference sensors 6 may reside at the proximal end of the apparatus and further proximal of the reference sensors 6 is infusion lumen 20 through which fluid or gas is passed to the member space 26 for inflation. FIG. 7B depicts the expandable member 10 advanced (optionally along) guidewire 12 distally of sheath 22 and residing, at least in partially expanded configuration, within target region 24. Alternatively, sheath 22 may be advanced into target region 24 and while a position of member 10 is maintained relative to region 24, sheath 22 may be proximally retracted to expose member 10 within region 24. In either case, once member 10 has been positioned within region 24, inflation fluid or gas may be infused into member 10 to expand it as well as the plurality of sensors into contact with the interior surfaces of region 24. Reference sensors 6 are proximal to the apparatus, and further proximal still is delivery sheath 22, and infusion lumen 20 which infuses the expandable member 10 with fluid or gas.

The applications of the disclosed invention discussed above are not limited to certain treatments or regions of the body, but may include any number of other treatments and areas of the body. Modifications of the above-described methods and devices for carrying out the invention, and variations of aspects of the invention that are obvious to those of skill in the arts are intended to be within the scope of this disclosure. Moreover, various combinations of aspects between examples are also contemplated and are considered to be within the scope of this disclosure as well.

What is claimed is:

1. An apparatus for characterization of a three-dimensional space in a target region within a mammalian body comprising:
   an expandable member having two or more transducers upon the expandable member and reference sensors positioned along a catheter body proximal to the expandable member and the two or more transducers, the expandable member deliverable in a deflated state to the target region having a volume, the member adapted to inflate in the target region to at least partially fill the volume of the target region;
   a fluid medium having a predetermined resistivity and which is in fluid communication with an interior of the expandable member, where the two or more transducers are in communication with one another through the medium when filled within the interior; and,
   a microprocessor configured to calculate a distance between the two or more transducers based on the predetermined resistivity of the medium determined from a known distance between the reference sensors.

2. The apparatus of claim 1, wherein sensory information sensed by the two or more transducers is relayed to the microprocessor located outside the body.

3. The apparatus of claim 2, the microprocessor having a mechanism for processing captured information selected from the group consisting of creating a shape of the target region, calculating a volume of the target region, display of shape information, display of volume information, display of captured information over time, measuring surface curvature, identifying contour variations, calculating volume, and subtracting an initial data set from a subsequent data set.

4. The apparatus of claim 1, the expandable member adapted to exceed the volume of the target region.

5. The apparatus of claim 1, further comprising a through-lumen for adapting the expandable member to slide over a guidewire.

6. The apparatus of claim 1, the expandable member adapted to fit within a steerable catheter in order to deliver the member to the target region.

7. The apparatus of claim 1, further comprising an external control mechanism.

8. The apparatus of claim 7, wherein the control mechanism controls a function selected from the group consisting of steering the member, inflating the member, deflating the member, and adjusting position of the transducers.

9. The apparatus of claim 1, wherein the transducers comprise a sensing mechanism selected from the group consisting of electrical impedance, ultrasound, optical sensing, and low-field electromagnetic sensing.

10. The apparatus of claim 9, the sensing mechanism comprising electrical impedance, the apparatus comprising at least one temperature sensor to monitor temperature in the medium.

11. The apparatus of claim 9, the sensing mechanism comprising low-field electromagnetic sensing, the transducers comprising internal coils placed in the expandable member relative to a magnetic field generated external to the body.

12. The apparatus of claim 1, further comprising a calibration mechanism for use as a reference point to calibrate the apparatus before receiving sensory information from the transducers.

13. The apparatus of claim 1, further comprising a control to maintain expanding pressure on the expandable member so that the apparatus can maintain its position within a space that is expanding.

14. The apparatus of claim 1 further comprising a display in communication with the microprocessor.

15. The apparatus of claim 14 wherein the microprocessor is programmed to visually display a corresponding image of the target region upon the display.

16. A method of assessing a three-dimensional character of a target region in a mammalian body, comprising:
   introducing into the body an expandable member adapted to inflate within the body, the expandable member having two or more transducers upon the expandable member and reference sensors positioned along a catheter body proximal to the expandable member and the two or more transducers, the expandable member deliverable in a deflated state to the target region having a volume, the member adapted to inflate in the target region to substantially fill the volume of the target region navigating the expandable member to the target region;
   inflating the expandable member with a fluid medium having a predetermined resistivity;
   detecting a parameter between the two or more transducers in correlation with the medium by transmitting a signal between the two or more transducers through the medium; and
   calculating the three-dimensional character of the target region via a microprocessor in communication with the two or more transducers based on the predetermined resistivity of the medium determined from a known distance between the reference sensors.

17. The method of claim 16, wherein the target region is selected from the group consisting of a heart, an abdominal aorta, a spinal column, a body orifice and an organ having a tumor.

18. The method of claim 17, the target region comprising the heart, the method adapted to perform a function selected from the group consisting of measuring the shape of a left atrial appendage, measuring the shape and size of a pulmonary vein ostia, and measuring the size and shape of a septal defect in an atrium or ventricle.

19. The method of claim 16 further comprising displaying the three-dimensional character of the target region upon a display for inspection by a user.

20. A system for characterization of a three-dimensional space within a mammalian body comprising:
   a delivery sheath comprising a deflated expandable member adapted to expand within a mammalian body,
   the expandable member having two or more transducers upon the expandable member and reference sensors positioned along a catheter body proximal to the expandable member and the two or more transducers,
   the expandable member deliverable to a target region having a volume,
   the member adapted to inflate in the target region to substantially fill the volume of the target region,
   a fluid medium having a predetermined resistivity and which is in fluid communication with an interior of the expandable member, where the two or more transducers are in communication with one another through the medium when filled within the interior; and, a microprocessor configured to calculate a distance between the two or more transducers based on the predetermined resistivity of the medium determined from a known distance between the reference sensors, where the microprocessor is located outside the body for receiving and processing sensory information sensed by the two or more transducers.

21. The system of claim 20, further comprising one or more control members for controlling one or more functions selected from the group consisting of delivery of the expandable member, inflation of the member, transducer sensing, and relay of sensory information.

22. The system of claim 20, wherein the expandable member further comprises a through-lumen for a guidewire.

23. The system of claim 20, further comprising a steerable catheter within which the expandable member is deliverable to the target region.

24. The system of claim 20, the microprocessor capable of recording captured information selected from the group consisting of a shape of the target region, a volume of the target region, display of shape information, display of volume information, display of information captured over time, measurement of surface curvature, measurement of volume, and subtracting an initial data set from a subsequent data set.

25. The system of claim 20 further comprising a display in communication with the microprocessor.

26. The system of claim 25 wherein the microprocessor is programmed to visually display a corresponding image of the target region upon the display.

* * * * *